(12) United States Patent
Kleiner et al.

(10) Patent No.: US 10,076,591 B2
(45) Date of Patent: *Sep. 18, 2018

(54) ABSORBABLE COATING FOR IMPLANTABLE DEVICE

(71) Applicant: Abbott Cardiovascular Systems Inc., Santa Clara, CA (US)

(72) Inventors: Lothar W. Kleiner, Los Altos, CA (US); Syed F. A. Hossainy, Hayward, CA (US); Mikael Trollsas, San Jose, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,973

(22) Filed: Jun. 24, 2016

(65) Prior Publication Data

US 2016/0303295 A1 Oct. 20, 2016

Related U.S. Application Data

(63) Continuation of application No. 14/182,211, filed on Feb. 17, 2014, now Pat. No. 9,387,282, which is a continuation of application No. 12/751,989, filed on Mar. 31, 2010, now Pat. No. 8,685,433.

(51) Int. Cl.
| | | |
|---|---|---|
| *A61L 31/10* | (2006.01) | |
| *A61L 31/14* | (2006.01) | |
| *A61L 31/16* | (2006.01) | |

(52) U.S. Cl.
CPC ............ *A61L 31/148* (2013.01); *A61L 31/10* (2013.01); *A61L 31/16* (2013.01); *A61L 2300/41* (2013.01); *A61L 2300/416* (2013.01); *A61L 2300/42* (2013.01); *A61L 2420/02* (2013.01); *A61L 2420/08* (2013.01)

(58) Field of Classification Search
CPC ........ A61L 31/10; A61L 31/148; A61L 31/16; A61L 2420/02; A61L 2300/42; A61L 2420/08; A61L 2300/41; A61L 2300/416; C08L 67/04
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 3,882,816 A | 5/1975 | Rooz et al. |
| 3,995,075 A | 11/1976 | Cernauskas et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,560,374 A | 12/1985 | Hammerslag |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,865,879 A | 9/1989 | Finlay |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,130,173 A | 7/1992 | Barten et al. |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,443,458 A | 8/1995 | Eury |
| 5,444,113 A | 8/1995 | Sinclair et al. |

(Continued)

FOREIGN PATENT DOCUMENTS

| | | |
|---|---|---|
| DE | 42 24 401 | 1/1994 |
| EP | 0 301 856 A2 | 2/1989 |

(Continued)

OTHER PUBLICATIONS

Alt et al., "Inhibition of neointima formation after experimental coronary artery Stenting: A New Biodegradable Stent Coating Releasing hirudin and the prostacyclin Analogue Ilopropst", *Circulation*, Mar. 28, 2000, vol. 101, pp. 1453-1458.

Butany et al., "Corinary artery stents: identification and evaluation", *J Clin Pathol.*, Aug. 2005, vol. 58, pp. 795-804.

Colombo et al., "Selection of Coronary Stents", *Journal of the America College of Cardiology*, 2002, vol. 40, No. 6, pp. 1021-1033.

Costa Jr et al., "Novolimus™-elulting coronary stent system", *Interv. Cardiol.* 2010, vol. 2, No. 5, pp. 645-649.

Degradable Polymers Principles and Applications 2nd Edition Edited by Gerald Scott; *Kluwer Academic Publishers*, 2002, pp. 321-329; ISBN 1-4020-0790-6.

Diener T et al., "Biodegradable Drug Depots on Coronary Stents—Local Drug Delivery in Interventional Cardiology", *Progress in Biomedical Research*, Jun. 2003, vol. 8, No. 2, pp. 82-91.

Hermann et al, "Antithrombogenic Coating of Stents Using a Biodegradable Drug Delivery Technology", *Thromb Haemost*, 1999, vol. 82, pp. 51-57.

(Continued)

*Primary Examiner* — David J Blanchard
*Assistant Examiner* — Daniel F. Coughlin
(74) *Attorney, Agent, or Firm* — Squire Patton Boggs (US) LLP

(57) ABSTRACT

The present invention provides an absorbable coating for an implantable device and the methods of making and using the same.

2 Claims, No Drawings

(56) References Cited

U.S. PATENT DOCUMENTS

| | | |
|---|---|---|
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,558,900 A | 9/1996 | Fan et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,161 A | 9/1997 | Healy et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,697 A | 3/1999 | Ding et al. |
| 5,879,713 A | 3/1999 | Roth et al. |
| 5,891,507 A | 4/1999 | Jayaraman |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,030,371 A | 2/2000 | Pursley et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,156,064 A | 12/2000 | Chouinard |
| 6,156,373 A | 12/2000 | Zhong et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,239,124 B1 | 5/2001 | Zenke et al. |
| 6,240,616 B1 | 6/2001 | Yan |
| 6,242,063 B1 | 6/2001 | Ferrera et al. |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,358,567 B2 | 3/2002 | Pham et al. |
| 6,364,903 B2 | 4/2002 | Tseng et al. |
| 6,368,658 B1 | 4/2002 | Schwarz et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,534,112 B1 | 3/2003 | Bouchier et al. |

(56) References Cited

U.S. PATENT DOCUMENTS

| | | |
|---|---|---|
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,363 B1 | 9/2003 | Li |
| 6,616,765 B1 | 9/2003 | Wu et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,939,376 B2 | 9/2005 | Shulze et al. |
| 7,220,755 B2 | 5/2007 | Betts et al. |
| 7,285,304 B1 | 10/2007 | Hossainy et al. |
| 7,431,959 B1 | 10/2008 | Dehnad |
| 7,524,528 B2 | 4/2009 | Kodas et al. |
| 7,682,387 B2 | 3/2010 | Shulze et al. |
| 7,727,275 B2 | 6/2010 | Betts et al. |
| 7,807,211 B2 | 10/2010 | Hossainy et al. |
| 7,867,988 B2 | 1/2011 | Yan et al. |
| 7,901,451 B2 | 3/2011 | Savage et al. |
| 8,021,678 B2 | 9/2011 | Hossainy et al. |
| 8,088,789 B2 | 1/2012 | Yan et al. |
| 8,182,890 B2 | 5/2012 | Zheng et al. |
| 8,252,046 B2 | 8/2012 | Shulze et al. |
| 8,252,047 B2 | 8/2012 | Savage et al. |
| 8,308,795 B2 | 11/2012 | Shulze et al. |
| 8,323,760 B2 | 12/2012 | Zheng et al. |
| 8,367,081 B2 | 2/2013 | Yan et al. |
| 8,404,641 B2 | 3/2013 | Yan et al. |
| 8,545,550 B2 | 10/2013 | Shulze et al. |
| 8,636,792 B2 | 1/2014 | Zheng et al. |
| 8,715,341 B2 | 5/2014 | Shulze et al. |
| 8,871,292 B2 | 10/2014 | Savage et al. |
| 8,952,123 B1 | 2/2015 | Ding |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0004564 A1 | 1/2003 | Elkins et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0125800 A1 | 7/2003 | Shulze et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2003/0236573 A1 | 12/2003 | Evans et al. |
| 2004/0018296 A1 | 1/2004 | Castro et al. |
| 2004/0029952 A1 | 2/2004 | Chen et al. |
| 2004/0030380 A1 | 2/2004 | Shulze et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0167572 A1 | 8/2004 | Roth et al. |
| 2004/0197372 A1 | 10/2004 | Llanos et al. |
| 2005/0037048 A1 | 2/2005 | Song |
| 2005/0079470 A1 | 4/2005 | Rutherford et al. |
| 2005/0131008 A1 | 6/2005 | Betts et al. |
| 2006/0093771 A1 | 5/2006 | Rypacek et al. |
| 2006/0229711 A1 | 10/2006 | Yan et al. |
| 2006/0246108 A1 | 11/2006 | Pacetti et al. |

(56) References Cited

U.S. PATENT DOCUMENTS

| | | |
|---|---|---|
| 2007/0027554 A1 | 2/2007 | Biran et al. |
| 2007/0078513 A1 | 4/2007 | Campbell |
| 2007/0155010 A1 | 7/2007 | Farnsworth et al. |
| 2008/0091262 A1 | 4/2008 | Gale et al. |
| 2008/0177373 A1 | 7/2008 | Huang et al. |
| 2009/0036978 A1 | 2/2009 | Kleiner et al. |
| 2009/0110713 A1 | 4/2009 | Lim et al. |
| 2009/0228094 A1 | 9/2009 | Yan et al. |
| 2009/0291111 A1 | 11/2009 | Lim et al. |
| 2010/0086579 A1 | 4/2010 | Yan et al. |
| 2010/0104734 A1 | 4/2010 | Orosa et al. |
| 2010/0256746 A1 | 10/2010 | Taylor et al. |
| 2010/0291175 A1 | 11/2010 | Trollsas et al. |
| 2011/0097364 A1 | 4/2011 | Yan et al. |
| 2012/0071500 A1 | 3/2012 | Yan et al. |
| 2012/0071962 A1 | 3/2012 | Huang et al. |
| 2012/0187606 A1 | 7/2012 | Zheng et al. |
| 2012/0283391 A1 | 11/2012 | Venkatraman et al. |
| 2013/0150943 A1 | 6/2013 | Zheng et al. |
| 2013/0230571 A1 | 9/2013 | Yan et al. |
| 2013/0331927 A1 | 12/2013 | Zheng et al. |
| 2014/0242144 A1 | 8/2014 | Sudhir et al. |
| 2015/0217029 A1 | 8/2015 | Ding et al. |
| 2015/0306282 A1 | 10/2015 | Scanlon et al. |
| 2015/0342764 A1 | 12/2015 | Ramzipoor et al. |
| 2015/0359943 A1 | 12/2015 | Roorda et al. |
| 2016/0263287 A1 | 9/2016 | Zhang et al. |

FOREIGN PATENT DOCUMENTS

| | | |
|---|---|---|
| EP | 0 396 429 A2 | 11/1990 |
| EP | 0 514 406 B1 | 3/1994 |
| EP | 0 604 022 A1 | 6/1994 |
| EP | 0 623 354 A1 | 11/1994 |
| EP | 0 665 023 A1 | 8/1995 |
| EP | 0 701 802 A1 | 3/1996 |
| EP | 0 716 836 A1 | 6/1996 |
| EP | 0 809 999 A2 | 12/1997 |
| EP | 0 832 655 A2 | 4/1998 |
| EP | 0 850 651 A2 | 7/1998 |
| EP | 0 879 595 A2 | 11/1998 |
| EP | 0 923 953 A2 | 6/1999 |
| EP | 0 953 320 A2 | 11/1999 |
| EP | 0 982 041 A1 | 3/2000 |
| EP | 1 023 879 A2 | 8/2000 |
| EP | 0 910 584 B1 | 7/2001 |
| EP | 1 273 314 A1 | 1/2003 |
| EP | 0 950 386 B1 | 7/2004 |
| EP | 0 970 711 B1 | 10/2004 |
| EP | 1 192 957 B1 | 2/2007 |
| EP | 1 689 754 B1 | 8/2007 |
| EP | 1 796 754 B1 | 10/2009 |
| EP | 2 113 230 A2 | 11/2009 |
| EP | 1 518 517 B1 | 12/2009 |
| EP | 2 123 311 B1 | 4/2012 |
| EP | 1 490 125 B2 | 6/2012 |
| EP | 1 505 930 B1 | 7/2014 |
| EP | 2 578 186 B1 | 7/2014 |
| EP | 2 417 943 B1 | 8/2014 |
| EP | 1 852 437 B1 | 9/2014 |
| EP | 2 316 377 B1 | 11/2014 |
| JP | 2001-190687 | 7/2001 |
| JP | 2007-130179 A | 5/2007 |
| JP | 2007-190369 A | 8/2007 |
| JP | 2010-507408 A | 5/2008 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/35575 | 10/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/50007 | 8/2000 |
| WO | WO 00/62830 | 10/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 01/87368 A1 | 11/2001 |
| WO | WO 02/03890 | 1/2002 |
| WO | WO 02/07601 A2 | 1/2002 |
| WO | WO 02/18477 A2 | 3/2002 |
| WO | WO 02/26162 | 4/2002 |
| WO | WO 02/34311 | 5/2002 |
| WO | WO 02/47731 A2 | 6/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 A1 | 10/2003 |
| WO | WO 03/090818 A2 | 11/2003 |
| WO | WO 04/000383 | 12/2003 |
| WO | WO 2004/009145 | 1/2004 |
| WO | WO 2004/026361 A1 | 4/2004 |
| WO | WO 2004/087045 A2 | 10/2004 |
| WO | WO 2005/051449 A1 | 6/2005 |
| WO | WO 2005/063319 A1 | 7/2005 |
| WO | WO 2008/098418 A1 | 8/2008 |
| WO | WO 2008/121702 A2 | 10/2008 |
| WO | WO 2009/018227 A2 | 2/2009 |
| WO | WO 2009/108490 A2 | 9/2009 |
| WO | WO 2009/142934 A2 | 11/2009 |
| WO | WO 2010/025406 A1 | 3/2010 |

OTHER PUBLICATIONS

Jain, Rajeev A. "The manufacturing techniques of various drug loaded biodegradeable poly (lactide-*co*-glycolide) (PLGA) devices," *Biomaterials*, (2000), vol. 21, No. 23, pp. 2475-2490.

Lee et al., "Synthesis and Degradation of End-Group-Functionalized Polylactide," *Journal of Polymer Science: Part A: Polymer Chemistry*, 2001, vol. 39, pp. 973-985.

Middleton et al.; "Synthetic biodegradable polymers as orthopedic devices", *Biomaterials*, 2000, vol. 21, pp. 2335-2346.

Panyam et al., "Polymer degradation in vitro release of a model protein from poly(D,L-lactide-co-glycolide) nano- and microparticles", *Journal of Controlled Release*, 2003, vol. 92, pp. 173-187.

Pillai et al., "PolAlners in drug delivery", *Current Opinion in Chemical Biology*, 2001, vol. 5, pp. 447-451.

Uhrich et al., "Polemerie Systems for Controlled Drug Release", *Chem. Rev.*, 1999, vol. 99, pp. 3191-3198.

Anonymous, "Cardiologists Draw-Up the Dream Stent", *Clinica* 710:15 (Jun. 17, 1996), http://www.dialogweb.com/cgi/document?req=1061848202959, printed Aug. 25, 2003 (2 pages).

(56) References Cited

OTHER PUBLICATIONS

Anonymous, "Heparin-coated stents cut complications by 30%", *Clinica* 732:17 (Nov. 18, 1996), http://www.dialogweb.com/cgi/document?req=1061847871753, printed Aug. 25, 2003 (2 pages).
Anonymous, "Rolling Therapeutic Agent Loading Device for Therapeutic Agent Delivery or Coated Stent" (Abstract 434009), *Res. Disclos.* pp. 974-975 (Jun. 2000).
Anonymous, "Stenting continues to dominate cardiology", *Clinica* 720:22 (Sep. 2, 1996), http://www.dialogweb.com/cgi/document?req=1061848017752, printed Aug. 25, 2003 (2 pages).
Aoyagi et al., "Preparation of cross-linked aliphatic polyester and application to thermo-responsive material", *Journal of Controlled Release* 32:87-96 (1994).
Barath et al., "Low Dose of Antitumor Agents Prevents Smooth Muscle Cell Proliferation After Endothelial Injury", *JACC* 13(2): 252A (Abstract) (Feb. 1989).
Barbucci et al., "Coating of commercially available materials with a new heparinizable material", *J. Biomed. Mater. Res.* 25:1259-1274 (Oct. 1991).
Chung et al., "Inner core segment design for drug delivery control of thermo-responsive polymeric micelles", *Journal of Controlled Release* 65:93-103 (2000).
Dev et al., "Kinetics of Drug Delivery to the Arterial Wall Via Polyurethane-Coated Removable Nitinol Stent: Comparative Study of Two Drugs", *Catheterization and Cardiovascular Diagnosis* 34:272-278 (1995).
Dichek et al., "Seeding of Intravascular Stents with Genetically Engineered Endothelial Cells", *Circ.* 80(5):1347-1353 (Nov. 1989).
Eigler et al., "Local Arterial Wall Drug Delivery from a Polymer Coated Removable Metallic Stent: Kinetics, Distribution, and Bioactivity of Forskolin", *JACC*, 4A (701-1), Abstract (Feb. 1994).
Forrester et al., "A Paradigm for Restenosis Based on Cell Biology: Clues for the Development of New Preventive Therapies", *J. Am. Coll. Cardio.* 1991; 17(3):758-769.
Helmus, "Overview of Biomedical Materials", MRS Bulletin, pp. 33-38 (Sep. 1991).
Herdeg et al., "Antiproliferative Stent Coatings: Taxol and Related Compounds", *Semin. Intervent. Cardiol.* 3:197-199 (1998).
Huang et al., "Biodegradable Polymers Derived from Aminoacids", *Macromol. Symp.* 144, 7-32 (1999).
Inoue et al., "An AB block copolymer of oligo(methyl methacrylate) and poly(acrylic acid) for micellar delivery of hydrophobic drugs", *Journal of Controlled Release* 51:221-229 (1998).
Kataoka et al., "Block copolymer micelles as vehicles for drug delivery", *Journal of Controlled Release* 24:119-132 (1993).
Katsarava et al., "Amino Acid-Based Bioanalogous Polymers. Synthesis and Study of Regular Poly(ester amide)s Based on Bis(α-amino acid)α,ω-Alkylene Diesters, and Aliphatic Dicarbolic Acids", *Journal of Polymer Science, Part A: Polymer Chemistry*, 37(4), 391-407 (1999).
Levy et al., "Strategies for Treating Arterial Restenosis Using Polymeric Controlled Release Implants", *Biotechnol. Bioact. Polym.* [Proc. Am. Chem. Soc. Symp.], pp. 259-268 (1994).
Liu et al., "Drug release characteristics of unimolecular polymeric micelles", *Journal of Controlled Release* 68:167-174 (2000).
Marconi et al., "Covalent bonding of heparin to a vinyl copolymer for biomedical applications", *Biomaterials* 18(12):885-890 (1997).
Matsumaru et al., "Embolic Materials for Endovascular Treatment of Cerebral Lesions", *J. Biomater. Sci. Polymer Edn* 8(7):555-569 (1997).
Miyazaki et al., "Antitumor Effect of Implanted Ethylene-Vinyl Alcohol Copolymer Matrices Containing Anticancer Agents on Ehrlich Ascites Carcinoma and P388 Leukemia in Mice", *Chem. Pharm. Bull.* 33(6) 2490-2498 (1985).
Miyazawa et al., "Effects of Pemirolast and Tranilast on Intimal Thickening After Arterial Injury in the Rat", *J. Cardiovasc. Pharmacol.*, pp. 157-162 (1997).
Nordrehaug et al., "A novel biocompatible coating applied to coronary stents", *EPO Heart Journal* 14, p. 321 (p. 1694), Abstr. Suppl. (1993).
Ohsawa et al., "Preventive Effects of an Antiallergic Drug, Pemirolast Potassium, on Restenosis After Percutaneous Transluminal Coronary Angioplasty", *American Heart Journal* 136(6):1081-1087 (Dec. 1998).
Ozaki et al., "New Stent Technologies", *Progress in Cardiovascular Diseases*, vol. XXXIX(2):129-140 (Sep./Oct. 1996).
Pechar et al., "Poly(ethylene glycol) Multiblock Copolymer as a Carrier of Anti-Cancer Drug Doxorubicin", *Bioconjucate Chemistry* 11(2):131-139 (Mar./Apr. 2000).
Peng et al., "Role of polymers in improving the results of stenting in coronary arteries", *Biomaterials* 17:685-694 (1996).
Saotome et al., "Novel Enzymatically Degradable Polymers Comprising α-Amino Acid, 1,2-Ethanediol, and Adipic Acid", *Chemistry Letters*, (1991), pp. 21-24.
Shigeno "Prevention of Cerebrovascular Spasm by Bosentan, Novel Endothelin Receptor", *Chemical Abstract* 125:212307 (1996); 2 pages.
van Beusekom et al., Coronary stent coatings, Coronary Artery Disease 5(7):590-596 (Jul. 1994).
Wilensky et al., Methods and Devices for Local Drug Delivery in Coronary and Peripheral Arteries, *Trends Cardiovasc. Med.* 3(5):163-170 (1993).
Yokoyama et al., "Characterization of physical entrapment and chemical conjugation of adriamycin in polymeric micelles and their design for in vivo delivery to a solid tumor", *Journal of Controlled Release* 50:79-92 (1998).
Pillai et al., "Polymers in drug delivery", *Current Opinion in Chemical Biology*, 2001, vol. 5, pp. 447-451.
Stefan Verheye, Antwerp Cardiovascular Institute ZNA Middelheim, Antwerp, Belgium, "Overview of Novolimus Elution and Myolimus Elution from Durable and Bioabsorbable Polymers", (2010), Cardio middelheim, 21 pages.
Yan et al., "Elixir Medical's bioresorbable drug eluting stent (BDES) programme: an overview", *EuroIntervention Supplement* (2009), vol. 5 (Supplement F), pp. F80-F82.

ABSORBABLE COATING FOR IMPLANTABLE DEVICE

CROSS-REFERENCE

This application is a continuation application of U.S. application Ser. No. 14/182,211, filed Feb. 17, 2014, which is a continuation of U.S. application Ser. No. 12/751,989, filed Mar. 31, 2010 (U.S. Pat. No. 8,685,433), the teaching of which are incorporated by reference herein.

FIELD OF THE INVENTION

The present invention relates to an absorbable coating an implantable device and methods of making and using the same.

BACKGROUND OF THE INVENTION

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

Problems associated with the above procedure include formation of intimal flaps or torn arterial linings which can collapse and occlude the blood conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of the arterial lining and to reduce the chance of thrombosis or restenosis, a stent is implanted in the artery to keep the artery open.

Drug eluting stents have reduced the incidence of in-stent restenosis (ISR) after PCI (see, e.g., Serruys, P. W., et al., J. Am. Coll. Cardiol. 39:393-399 (2002)), which has plagued interventional cardiology for more than a decade. However, a few challenges remain in the art of drug eluting stents. For example, compromised coating integrity when an amorphous bioabsorbable polymer is used for coating a stent, which can result from the conditions of ethylene oxide (ETO) sterilization or from the conditions of crimping a stent onto the delivery balloon. Conditions such as elevated temperature, high relative humidity, and high concentration of ETO in the ETO sterilization process can result in plasticization and adhesion of the coating to the balloon via polymer deformation and flow. In a similar way, a completely amorphous bioabsorbable polymer may flow when crimped at temperatures above the polymer glass transition temperature ($T_g$) on to the delivery balloon.

Aliphatic polyesters are used in pharmaceutical and biomedical applications, including for example surgical sutures and drug delivery systems. Poly(L-lactide) (PLLA) is one of the most widely studied polymer biomaterials, attractive for its biodegradable and biocompatible properties. However, PLLA is not ideally suited for many aspects of drug delivery systems, including those involving drug-eluting stents. Issues of L-lactide based drug delivery stent systems include compromised mechanical properties after the fabrication process and deployment of such systems, and a sometimes relatively long absorption period.

The embodiments of the present invention address the above-identified needs and issues.

SUMMARY OF THE INVENTION

In one aspect, the present invention provides a bioabsorbable coating on an implantable medical device. The coating comprises a primer layer comprising a bioabsorbable polymer having a first molecular weight and a second layer comprising a bioabsorbable polymer of a second molecular weight. The first molecular weight is higher than the second molecular weight, and the coating is completely or substantially completely absorbed upon implantation in a human body within a period from about 3 months to about 6 months.

In some embodiments, the primer layer comprises a high or very high molecular weight (HMW or VHMW) absorbable polymer. Examples of such HMW or VHMW absorbable polymer are PLLA, 85/15 PLGA, 75/25 PLGA, poly (ester amide), PLA-PCL-GA terpolymer, PCL-GA, and copolymers thereof.

In some embodiments, optionally in combination with the various embodiments above, the second layer comprises a low molecular weight (LMW) absorbable polymer. An example of the LMW absorbable polymer is LMW D,L-PLA.

In some embodiments, optionally in combination with the various embodiments above, the second layer comprises a drug or a drug embedded in an absorbable polymer.

In some embodiments, optionally in combination with the various embodiments above, the second layer does not comprise a drug and is formed on top of a layer of a drug on top of the primer layer.

In some embodiments, optionally in combination with the various embodiments above, the coating disclosed herein is micro-porous and is formed by a process of controlled phase inversion kinetics, wherein the second layer and/or the primer layer can include D,L-PLA.

In some embodiments, optionally in combination with the various embodiments above, the implantable device is a stent.

In some embodiments, optionally in combination with the various embodiments above, the second layer comprises a drug selected from the group consisting of are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, feno fibrate, prodrugs thereof, co-drugs thereof, and combinations thereof.

In another aspect, the present invention provides a method of fabricating an implantable device. The method comprises:
  forming a primer layer on surface of an implantable device comprising a high molecular weight (HMW) or very high molecular weight (VHMW) absorbable polymer; and
  forming a second layer comprising a low molecular weight (LMW) absorbable polymer, thereby forming the coating, wherein the first molecular weight is higher than the second molecular weight, wherein the coating is completely or substantially completely absorbed upon implantation in a human body within a period from about 3 months to about 6 months.

In some embodiments, the primer layer comprises a high or very high molecular weight (HMW or VHMW) absorbable polymer. Examples of such BMW or VHMW absorbable polymer are PLLA, 85/15 PLGA, 75/25 PLGA, poly (ester amide), PLA-PCL-GA terpolymer, PCL-GA, and copolymers thereof.

In some embodiments, optionally in combination with the various embodiments above, the second layer comprises a low molecular weight (LMW) absorbable polymer. An example of the LMW absorbable polymer is LMW D,L-PLA.

In some embodiments, optionally in combination with the various embodiments above, the second layer comprises a drug.

In some embodiments, optionally in combination with the various embodiments above, the second layer does not comprise a drug and is formed on top of a layer of a drug on top of the primer layer.

In some embodiments, optionally in combination with the various embodiments above, the coating disclosed herein is micro-porous and is formed by a process of controlled phase inversion kinetics, wherein the second layer and/or the primer layer can include D,L-PLA.

In some embodiments, optionally in combination with the various embodiments above, the implantable device is a stent.

In some embodiments, optionally in combination with the various embodiments above, the second layer comprises a drug selected from the group consisting of are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, novolimus, myolimus, temsirolimus, deforolimus, γ-hiridun, clobetasol, pimecrolimus, imatinib mesylate, midostaurin, feno fibrate, prodrugs thereof, co-drugs thereof, and combinations thereof.

In some embodiments, optionally in combination with the various embodiments above, the method further comprises enhancing the degradation rate of the coating, which enhancing degradation rate can be, for example, decreasing the molecular weight of the bioabsorbable polymer in the first and/or second post coating prior to deployment of the implantable device, or enhancing the rate of hydrolysis of the bioabsorbable polymer in the first and/or second layer.

In some embodiments, optionally in combination with the various embodiments above, enhancing the degradation rate of the coating comprises a step selected from:
  i) prolonged e-beaming, multiple e-beaming post coating, e-beaming at a lower dose rate for a total longer time under the beam, or e-beaming at room temperature;
  ii) higher temperature treatment of a coated implantable device for longer time drying in a high humidity environment prior to vacuum/conventional drying;
  iii) decreasing the BHT content in the coating if the coating comprises BHT;
  iv) adding lactide monomers and/or oligomers in the coating;
  v) adding -COOH terminated oligomers of D,L-PLA in the coating;
  vi) sterilization by gamma radiation at the same dose (i.e. 31 kGy) as would be used for e-beam;
  vii) adding in the coating a plasticizer selected from ethyl lactate, DMSO, NMP, and benzyl benzoate so as to lower the glass transition temperature ($T_g$) of the coating to accelerate degradation;
  viii) adding a hygroscopic additive in a coating;
  ix) adding micronized $NaO_2$ or $KO_2$, or superoxide salts in the coating;
  x) adding more stannous octoate to bring its level up to the maximum level allowed by the material specification;
  xi) adding LMW D,L-PLA with a MW tuned to degrade within 3 to 6 months;
  xii) forming micro-porous D,L-PLA coating by a process of controlled phase inversion kinetics; and
  xiii) any combination of step i)-xii).

In a still further aspect of the present invention, it is provided a method of treating, preventing, or ameliorating a vascular medical condition, comprising implanting in a patient an implantable medical comprising any of the implantable article described above. The vascular medical condition can be restenosis, atherosclerosis, thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

In one aspect, the present invention provides a bioabsorbable coating on an implantable medical device. The coating has an absorption period from about three months to about six months during which the coating is completely or substantially completely absorbed upon implantation in a human body. The coating comprises a primer layer on surface of the implantable device comprising a bioabsorbable polymer having a first molecular weight and a second layer comprising a bioabsorbable polymer of a second molecular weight, where the first molecular weight is higher than the second molecular weight. In some embodiments, the coating comprises a primer layer comprising a high or very high molecular weight (HMW or VHMW) absorbable polymer; and a second layer comprising a low molecular weight (LMW) absorbable polymer. The second layer can be a topcoat on top of a layer of a drug or a matrix layer where the matrix layer may or may not include a drug. In some embodiments, the matrix layer can include a drug.

In a second aspect, the present invention provides a method of fabricating an implantable device. The method comprises providing an implantable device and forming a coating on the implantable device. The coating has an absorption period from about three months to about six months during which the coating is completely or substantially completely absorbed upon implantation in a human body. The coating comprises a primer layer on surface of the implantable device comprising a bioabsorbable polymer having a first molecular weight and a second layer comprising a bioabsorbable polymer of a second molecular weight, where the first molecular weight is higher than the second molecular weight. In some embodiments, forming a coating comprises: a) forming a primer layer on surface of the implantable device comprising a HMW or VHMW absorbable polymer; b) forming a second layer comprising a LMW absorbable polymer, thereby forming the coating. The second layer can be a topcoat on top of a layer of a drug or a matrix layer where the matrix layer may or may not include a drug. In some embodiments, the matrix layer can include a drug.

Suitable HMW absorbable polymer as primer generally has high elongation. Examples of such HMW absorbable polymers include, e.g., VHMW PLLA, 85/15 PLGA, HMW or VHMW 75/25 PLGA, HMW or VHMW poly(ester amide) (elastomeric), HMW or VHMW PLA-PCL-GA terpolymer, HMW or VHMW PCL-GA, or copolymers thereof. Additional examples include poly(β-hydroxybutyrate) (PHB), copolymers of 3-hydroxybutyrate (3HB) and 3-hyroxyvalerate (3HV), random copolymers of 3HB and 4HV, polycarbonates, polyanhydrides, poly(phosphate esters), polyphosphazenes, and poly(orthoesters).

As used herein, the term HMW refers to a molecular weight about 60,000 Daltons and below about 200,000 Daltons. The term VHMW refers to a molecular weight about 200,000 Daltons or above. Conversely, the term LMW refers to a number average molecular weight below 60,000 Daltons, e.g., 57,000 Daltons.

In some embodiments, optionally in combination with any one or combinations of the above embodiments, the method further comprises increasing the rate of absorption of the coating described above by decreasing the molecular weight of the polymer in the coating. Decreasing the molecular weight of the polymer in the coating can be achieved by various established methods. Such methods, which are described in detail below, include, for example, a prolonged e-beam process post coating to decrease the molecular weight of the polymer in the coating. In some embodiments, such method includes, e.g., selecting a commercial polymer of a desired molecular weight or a commercial absorbable polymer having an acid end group, and forming the second layer using commercial polymer.

In some embodiments, optionally with one or any combination of features of the various embodiments above, the stent or the coating further comprises a bioactive agent. Examples of the bioactive agent are paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), zotarolimus, myolimus, novolimus, temsirolimus, deforolimus, γ-hiridun, clobetasol, pimecrolimus, imatinib mesylate, midostaurin, feno fibrate, prodrugs thereof, co-drugs thereof, and combinations thereof.

The implantable article described herein is generally degradable or bioabsorbable. In some embodiments, the coating can degrade within about 1 month, 2 months, 3 months, 4 months, or 6 months after implantation of an implantable device comprising the coating.

In some embodiments, the implantable article (e.g., an implantable medical device or a coating on an implantable medical device such as stent) can include one or more other biocompatible polymers, which are described below.

The implantable device described herein, such as a stent, can be implanted in a patient to treat, prevent, mitigate, or reduce a vascular medical condition, or to provide a pro-healing effect. In some embodiments, the vascular medical condition or vascular condition is a coronary artery disease (CAD) and/or a peripheral vascular disease (PVD). Some examples of such vascular medical diseases are restenosis and/or atherosclerosis. Some other examples of these conditions include thrombosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are sometimes used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. In some embodiments, a distinction can be made between bioresorbable and bioabsorbable where a bioresorbable polymer refers to one whose degradants the body can use whereas a bioabsorbable polymer refers to one whose degradants the body eliminates. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

As used herein, the term "complete degradation" or "completely degrade" shall be the state of full degradation or absorption of the coating. The term "substantially complete degradation" or "substantially completely degrade" shall mean a state of degradation where at least 80% of the coating is degraded, absorbed, or eroded. In some embodiments, "substantially complete degradation" or "substantially completely degrade" shall mean about 80% to about 99%, about 85% to about 99%, about 90% to about 99%, or about 95% to about 99% by weight of a coating is degraded, absorbed, or eroded.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal."

As used herein, the term "micro-porous" refers to a coating micro-scale pores, depots, channels, or cavity. The coating can have a porosity from about 5% to about 50%, from about 5% to about 40%, from about 10% to about 50%, from about 10% to about 40%, from about 10% to about 30%, from about 10% to about 20%, from about 20% to about 50%, from about 20% to about 40%, from about 20% to about 30%, from about 30% to about 50%, from about 30% to about 40%, or from about 40% to about 50% by volume. Specific examples of porosity in such a coating can be about 10%, about 20%, about 30%, about 40%, or about 50% by volume. The higher the porosity, the higher the rate of water uptake and the higher the equilibrium water content. This results in an enhanced rate of hydrolysis of the coating.

In the context of a blood-contacting implantable device, a "prohealing" drug or agent refers to a drug or agent that has the property that it promotes or enhances re-endothelialization kinetics of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.,* 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.,* 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs,* 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device.

As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, shunts, catheters, other expandable tubular devices for various bodily lumen or orifices, grafts, vascular grafts, arteriovenous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Decreasing Molecular Weight

The molecular weight of polymer forming the coating described herein can be reduced or decreased by various methods. The molecular weight can be decreased post coating of an implantable device prior to deployment of the implantable device (t=0) or after implantation of implantable device, e.g., by enhanced hydrolysis of the coating. Such methods include, e.g., one or a combination of the following:

1) prolonged e-beaming, multiple e-beaming post coating, e-beaming at a lower dose rate for a total longer time under the beam, or e-beaming at room temperature.

2) higher temperature treatment (e.g., treatment at 50° C. to 70° C.) of coated device (e.g., stent) for drying in a high humidity environment prior to vacuum/conventional drying. As used herein, the term "high humidity environment" refers to an environment having a degree of humidity higher than the ambient.

3) decreasing the BHT content in the coating.

4) addition of lactide monomers/oligomers in the coating.

5) addition of —COOH terminated oligomers of d,l PLA.

6) sterilization by gamma radiation at the same dose (i.e. 31 kGy) as would be used for e-beam.

6) addition of other plasticizers to the coating, e.g., ethyl lactate, DMSO, NMP, benzyl benzoate, which would lower the glass transition temperature ($T_g$) of the coating to accelerate degradation.

7) addition of a hygroscopic additive to the coating to increase water adsorption of D,L-PLA, if present, which hygroscopic additives can be, e.g., low MW PVP, low MW PEG. A higher water concentration in the coating increases hydrolysis rate, and the presence of water during irradiation sterilization will accelerate MW decrease in this step. Hygroscopic additive could be amphiphilic to allow better homogenicity.

8) addition of micronized $NaO_2$ or $KO_2$, or superoxide salts. These compounds are insoluble in organics but will cleave ester bonds quite actively when hydrated so as to decrease MW of the polymer in the coating.

9) addition of more stannous octoate to bring its level up to the maximum level allowed by the material specification. Stannous octate will increase MW drop during extrusion, e-beam sterilization, and in-vivo deployment.

10) addition of LMW D,L-PLA with a MW tuned to degrade within 3 to 6 months. Generally, such a LMW D,L-PLA would not form a coating of integrity. A primer formed of a HMW or VHMW resorbable polymer would make such a deficiency of the LMW D,L-PLA to allow forming a coating using such a LMW D,L-PLA. LMW D,L-PLA that degrades within 3 to 6 months generally have a molecular weight of below 60,000 Da.

11) forming micro-porous D,L-PLA coating by a process of controlled phase inversion kinetics. Such a micro-porous D,L-PLA coating allows for enhanced water uptake so as to increase hydrolysis of the coating. Phase inversion is within the general knowledge in the art since it is a commercially available process (used to fabricate membrane filters).

Biologically Active Agents

In some embodiments, the implantable device described herein can optionally include at least one biologically active ("bioactive") agent. The at least one bioactive agent can include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In certain embodiments, optionally in combination with one or more other embodiments described herein, the implantable device can include at least one biologically active agent selected from antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), ABT-578, novolimus, myolimus, deforolimus, temsirolimus, prodrugs thereof, co-drugs thereof, and combinations thereof. An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent can be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents can be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that can also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO). Other bioactive agents include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that can be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.*, 70A:10-19 (2004). Endothelial cells can be selectively targeted (for the targeted delivery of immunoliposomes) using scFv A5. T. Volkel, et al., *Biochimica et Biophysica Acta*, 1663:158-166 (2004). Junction membrane protein vascular endothelial (VE)-cadherin has been shown to bind to endothelial cells and down regulate apoptosis of the endothelial cells. R. Spagnuolo, et al., *Blood*, 103:3005-3012 (2004).

In a particular embodiment, the EDC-binding agent can be the active fragment of osteopontin, (Asp-Val-Asp-Val-Pro-Asp-Gly-Asp-Ser-Leu-Ala-Try-Gly). Other EDC-binding agents include, but are not limited to, EPC (epithelial cell) antibodies, RGD peptide sequences, RGD mimetics, and combinations thereof.

In further embodiments, the prohealing drug or agent can be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the implantable device of the invention comprises at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), ABT-578, novolimus, myolimus, temsirolimus, deforolimus, pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is dexamethasone acetate.

An alternative class of drugs would be p-para-α-agonists for increased lipid transportation, examples include fenofibrate.

In some embodiments, optionally in combination with one or more other embodiments described herein, the at least one biologically active agent specifically cannot be one or more of any of the bioactive drugs or agents described herein.

Coating Construct

According to some embodiments of the invention, optionally in combination with one or more other embodiments described herein, a coating disposed over an implantable device (e.g., a stent) can have a construct of any design. The coating can be a multi-layer structure that includes at least one primer layer described herein, which is layer (1) described below, and at least one reservoir layer, which is layer (2) described below, and can include any of the following (3), (4) and (5) layers or combination thereof:

(1) a primer layer;
(2) a reservoir layer (also referred to "matrix layer" or "drug matrix"), which can be a drug-polymer layer including at least one polymer (drug-polymer layer) or, alternatively, a polymer-free drug layer;
(3) a release control layer (also referred to as a "rate-limiting layer");
(4) a topcoat layer; and/or
(5) a finishing coat layer which is present to modulate the biological response the coating In some embodiments, a coating of the invention can include two or more reservoir layers described above, each of which can include a bioactive agent described herein.

Each layer of a coating can be disposed over the implantable device (e.g., a stent) by dissolving the inventive polymer mixture or block copolymer, optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to allow for crystallization of the polymer coating, to finish physical aging of the polymer, and/or to improve the thermodynamic stability of the coating.

To incorporate a bioactive agent (e.g., a drug) into the reservoir layer, the drug can be combined with the polymer solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied indirectly over at least a portion of the stent surface to serve as a reservoir for at least one bioactive agent (e.g., drug) that is incorporated into the reservoir layer over at least a portion of the primer layer. The primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, autoclaving, and gamma irradiation. Some of these processes can involve an elevated temperature or can be performed cold below room temperature. For example, ETO sterilization of a coated stent generally involves heating above 50° C. at humidity levels reaching up to 100% for periods of a few hours up to 24 hours. A typical ETO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

If neither a finishing coat layer nor a topcoat layer is used, the stent coating could have only two layers—the primer and the reservoir.

Any layer of a coating, except for the primer layer, can contain any amount of bioresorbable, erodible or biodissolvable polymers. Non-limiting examples of such polymers include bioabsorbable polymers and biocompatible polymers include poly(N-vinyl pyrrolidone); polydioxanone; polyorthoesters; polyanhydrides; poly(glycolic acid); poly(glycolic acid-co-trimethylene carbonate); polyphosphoesters; polyphosphoester urethanes; poly(amino acids); poly(trimethylene carbonate); poly(iminocarbonates); co-poly(ether-esters); polyalkylene oxalates; polyphosphazenes; biomolecules, e.g., fibrin, fibrinogen, cellulose, cellophane, starch, collagen, hyaluronic acid, and derivatives thereof (e.g., cellulose acetate, cellulose butyrate, cellulose acetate butyrate, cellulose nitrate, cellulose propionate, cellulose ethers, and carboxymethyl cellulose), polyurethane, polyesters, polycarbonates, polyurethanes, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid (PLLA-GA), poly(DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), or any copolymers thereof.

Method of Fabricating Implantable Device

Other embodiments of the invention, optionally in combination with one or more other embodiments described herein, are drawn to a method of fabricating an implantable device. In one embodiment, the method comprises forming the implantable device of a material containing a biodegradable polymer or copolymer.

Under the method, a portion of the implantable device or the whole device itself can be formed of the material containing a biodegradable polymer or copolymer. The method can deposit a coating having a range of thickness over an implantable device. In certain embodiments, the method deposits over at least a portion of the implantable device a coating that has a thickness of ≤about 30 microns, or ≤about 20 microns, or ≤about 10 microns, or ≤about 5 microns.

In certain embodiments, the method is used to fabricate an implantable device selected from stents, grafts, stent-grafts, catheters, leads and electrodes, clips, shunts, closure devices, valves, and particles. In a specific embodiment, the method is used to fabricate a stent.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus. In yet another embodiment, a bioabsorbable implant can be fabricated by weaving fibers of bioabsorbable materials.

Non-limiting examples of polymers that can be used to fabricate an implantable device include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(L-lactic acid-co-caprolactone) (PLLA-CL), poly(D-lactic acid-co-caprolactone) (PDLA-CL), poly(DL-lactic acid-co-caprolactone) (PDLLA-CL), poly(D-lactic acid-glycolic acid (PDLA-GA), poly(L-lactic acid-glycolic acid) (PLLA-GA), poly(DL-lactic acid-glycolic acid (PDLLA-GA), poly(L-lactic acid-co-caprolactone) (PLLA-CL), poly(D-lactic acid-co-caprolactone) (PDLA-CL), poly(DL-lactic acid-co-caprolactone) (PDLLA-CL), poly(glycolide-co-caprolactone) (PGA-CL), poly(thioesters), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), poly(vinylidene fluoride), poly(vinylidene fluoride-co-hexafluoropropylene), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose and derivates thereof (e.g., cellulose acetate, cellulose butyrate, cellulose acetate butyrate, cellophane, cellulose nitrate, cellulose propionate, cellulose ethers, and carboxymethyl cellulose), and copolymers thereof.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device is formed of a material or includes a coating containing at least one biologically active agent selected from paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), ABT-578, novolimus, myolimus, temsirolimus, deforolimus, pimecrolimus, imatinib mesylate, midostaurin, clobetasol, progenitor cell-capturing antibodies, prohealing drugs, fenofibrate, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

The invention claimed is:

1. A medical device, comprising:
   (a) a bio-absorbable stent body; and
   (b) a coating layer, the coating layer consists of D,L-PLA, novolimus, and BHT, wherein
      (i) the D,L-PLA has a number average molecular weight below 60,000 Daltons, and
      (ii) the coating layer has a thickness of less than 5 microns and has an absorption period from about 3 months to about 6 months, and
   wherein the stent body comprises poly(L-lactic acid-co-caprolactone) (PLLA-CL), poly(D-lactic acid-co-caprolactone) (PDLA-CL), poly(DL-lactic acid-co-caprolactone) (PDLLA-CL), poly(lactide-co-glycolide) (PLA-GA), poly(D-lactic acid-glycolic acid) (PDLA-GA), poly(L-lactic acid-glycolic acid) (PLLA-GA), poly(DL-lactic acid-glycolic acid (PDLLA-GA), or poly(glycolide-co-caprolactone) (PGA-CL).

2. A medical device of claim 1, wherein the coating layer is annealed at a temperature between about 40 deg. C. and about 150 deg. C.

* * * * *